US005522879A

United States Patent [19]

Scopelianos

[11] Patent Number: 5,522,879

[45] **Date of Patent: * Jun. 4, 1996**

[54] PIEZOELECTRIC BIOMEDICAL DEVICE

[75] Inventor: Angelo G. Scopelianos, Whitehouse Station, N.J.

[73] Assignee: Ethicon, Inc., Somerville, N.J.

[ * ] Notice: The term of this patent shall not extend beyond the expiration date of Pat. No. 5,311,884.

[21] Appl. No.: 199,365

[22] Filed: Feb. 18, 1994

Related U.S. Application Data

[63] Continuation-in-part of Ser. No. 959,500, Oct. 9, 1992, Pat. No. 5,311,884, which is a continuation-in-part of Ser. No. 790,810, Nov. 12, 1991, abandoned.

[51] Int. Cl.$^{6}$ .......... A61F 2/06

[52] U.S. Cl. .......... 623/1; 623/11; 623/12; 602/41; 602/42; 128/898; 606/152

[58] Field of Search .......... 128/898; 600/36; 602/41, 42, 58; 606/152; 623/1, 11, 12

[56] References Cited

U.S. PATENT DOCUMENTS

| | | | |
|---|---|---|---|
| 3,044,497 | 7/1962 | Rebut . | |
| 4,043,331 | 8/1977 | Martin et al. . | |
| 4,552,707 | 11/1985 | How . | |
| 4,564,013 | 1/1986 | Lilenfeld . | |
| 4,657,793 | 4/1987 | Fisher . | |
| 4,668,449 | 5/1987 | Soni et al. . | |
| 4,734,228 | 3/1988 | Micheron . | |
| 4,743,252 | 5/1988 | Martin et al. . | |
| 4,778,867 | 10/1988 | Preis . | |
| 4,798,607 | 1/1989 | Middleton et al. . | |
| 5,030,225 | 7/1991 | Aebischer . | |
| 5,160,870 | 11/1992 | Carson et al. | 310/339 |
| 5,311,884 | 5/1994 | Scopelianos | 623/1 |

FOREIGN PATENT DOCUMENTS

| | | |
|---|---|---|
| 0223374A1 | 10/1986 | European Pat. Off. . |
| 0239339 | 3/1987 | European Pat. Off. . |
| 2181207 | 4/1985 | United Kingdom . |

OTHER PUBLICATIONS

Japan. J. Appl. Phys. 8, (1969), The Piezoelectricity of Poly (vinylidene Fluoride) Heiju Kawai, 975–976.

Lovinger, Science, Ferroelectric Polymers, vol. 220, No. 4602, pp. 1115–1121.

*Primary Examiner*—Paul B. Prebilic
*Attorney, Agent, or Firm*—Hal Brent Woodrow

[57] ABSTRACT

A piezoelectric medical device prepared by electrostatically spinning a copolymer of vinylidene fluoride and a second fluorinated hydrocarbon, and collecting the spun fibers on a suitable receiver. The medical device can be in the form of a vascular prosthesis, neural prosthesis, or wound dressing and the copolymer can be composed of a predominant amount of vinylidene fluoride.

8 Claims, 2 Drawing Sheets

1
2
3
4
5
6
7

EHT 11
10

PIEZOELECTRIC BIOMEDICAL DEVICE

BACKGROUND OF THE INVENTION

This is a continuation-in-part application of Ser. No. 07/959,500 filed Oct. 9, 1992, the text of which is hereby incorporated by reference, now U.S. Pat. No. 5,311,884 which is a continuation-in-part of Ser. No. 790,810 filed Nov. 12, 1991 now abandoned.

This invention relates to biomedical devices. More particularly, it relates to such devices exhibiting piezoelectric properties which are prepared by electrostatically spinning certain fluorinated polymers.

Medical devices, and in particular vascular grafts, have been prepared from polymer compositions using electrostatic spinning techniques. These techniques are well known and described, for example, in U.S. Pat. Nos. 4,043,331; 4,552,707; 4,798,607 and 4,657,793; U.K. Patent Application GB 2,181,207, and European Patent Application Nos. 0 223 374 and 0 239 339. The polymers which can be spun include polyurethanes and fluorinated hydrocarbons such as polytetrafluoroethylene (PTFE). These polymers can be spun to prepare tubular structures suitable for vascular grafts, as well as fibrous mats or sheets suitable for use in wound dressings.

The polymers electrostatically spun to-date to prepare biomedical devices do not exhibit piezoelectric properties. A polymer is piezoelectric if it can convert mechanical energy or pressure into electrical energy, or vice-versa. In physical terms, piezoelectricity has been defined as the electrical polarization or charge produced by a mechanical strain in certain materials.

Through the use of selected polymeric materials, medical devices exhibiting piezoelectric properties and prepared by the electrostatic spinning technique are expected to display good biocompatibility, nonthrombogenicity, controlled porosity, oxygen and vapor transmission, and outstanding physical properties. In the body, the "piezoelectric effect" will be generated repeatedly by the effect of bodily movement upon the device. For example, when the device is a vascular graft, the regular beating of the heart and the pulsation of the blood vessels will act to provide the necessary mechanical strain on the device to induce the piezoelectric effect.

Certain piezoelectric polymers have been known for some time. For example, polyvinylidene fluoride and certain copolymers derived from vinylidene fluoride are piezoelectric. See Kawai H.:"The Piezoelectricity of Polyvinylidene Fluoride", Jpn. J. Appl. Phys. *:975, 1969, and Lovinger A.: "Ferroelectric Polymers", Science, Vol. 220, No. 4602, 1983. These piezoelectric polymers have found wide interest and acceptance in electronics, computer, avionics and audio and visual applications. Piezoelectric devices for these applications have been prepared conventionally as follows: a) the polymer is melt extruded to prepare a film, b) the melt extruded polymeric film is then subjected to a series of mechanical stresses or forces to induce an all-trans molecular conformation, and c) the stretched film is subjected to high voltage, plasma or corona poling to align the dipoles of each chain of the polymer in the direction of the field and induce an electrostatic charge. Steps b) and c) of this process are often referred to as "sequential stretching and poling".

While polymeric devices exhibiting piezoelectricity have found use for numerous applications, such devices have not been disclosed for biomedical applications. Furthermore, the conventional process for preparing piezoelectric devices, including stretching and poling of the device, limits the device to very specific geometries and forms, i.e., film or fiber, and is cumbersome, expensive and time-consuming. It would be extremely desirable to fabricate biomedical devices of various geometrical forms and exhibiting piezoelectric properties using a relatively simple and straightforward process.

BRIEF DESCRIPTION OF THE FIGURES

FIG. 1 is an earthed metal syringe needle supplied from a reservoir with spinning material at a rate related to the rate of fiber production. Belt 2 is of gauze, driven by a driving roller 3 and an idle roller 4 to which is fed an electrostatic charge from a generator 5 (in the apparatus illustrated a Van de Graaff machine). The fibers that are spun form a fiber mat 6 on belt 2. Roller 7 rotates against belt 2 and picks up the fiber mat 6.

SUMMARY OF THE INVENTION

Figure 1:
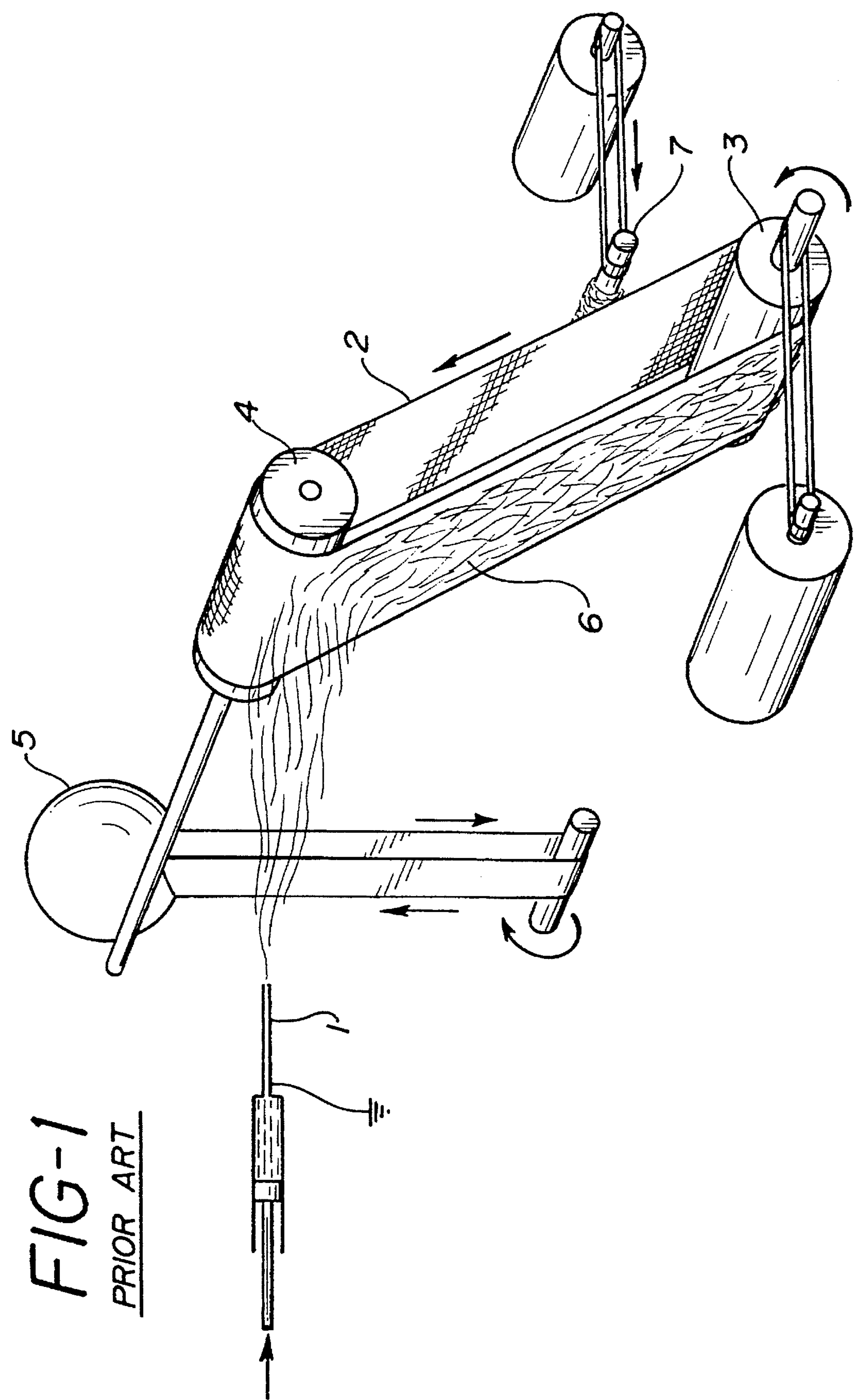
FIG. 1 is a diagrammatic view of an apparatus for electrostatically spinning and collecting fibers. In this

The invention is a biomedical device exhibiting piezoelectricity. The device is prepared by electrostatically spinning a copolymer of: a) a predominant amount of vinylidene fluoride, and b) a second fluorinated hydrocarbon. The fibers spun from the copolymer are collected on a suitable receiver.

Surprisingly, the device of this invention exhibits piezoelectric properties without the need for processing steps in addition to conventional electrostatic spinning. For example, the device does not require sequential stretching or poling to induce piezoelectricity. The device also exhibits outstanding physical properties regardless of its final physical form. The device can be in the form of a tubular structure, a fibrous mat or sheet, or any other form that can be created by electrostatic spinning which is suitable for biomedical applications.

The biomedical device of this invention can be used for numerous medical applications, including, but not limited to, synthetic vascular prosthesis, neural prostheses, cell culturing techniques, wound dressings, controlled drug-release formulations, and diagnostic applications.

DETAILED DESCRIPTION OF THE INVENTION

A biomedical device refers to a device used in or for the diagnosis, monitoring, treatment or prevention of disease, sickness or other physical condition. For example, biomedical devices of this invention can exist in the form of tubular structures such as vascular prothesis and prostheses for nerve regeneration, or as a fibrous sheet for wound dressing applications or membranes for bioseparations. Alternatively, the device can be shaped to form any structure particularly adapted for a desired application. Preferably, the device is in the form of a vascular prothesis or a wound dressing. The most preferred device is in the form of a vascular prothesis.

A device is piezoelectric if it exhibits the ability to generate a transient electrical charge when the device is mechanically stressed, e.g. compressed, extended or flexed in any manner. This transient charge supplements the permanent electrical charge which the device may exhibit upon fabrication using the electrostatic spinning process.

Electrostatic spinning of polymers and polymer compositions to prepare various geometric configurations suitable for biomedical devices is a well known technique. The details for the spinning technique can be found, most notably, in U.S. Pat. No. 4,043,331, incorporated by reference herein. Generally, a solution of the desired polymer in a compatible solvent is discharged from at least one nozzle onto an electrostatically-charged surface, or receiver. The polymer forms a fibrous structure conforming to the shape of the receiver. The receiver can be of any shape desired, and will depend on the shape desired for the biomedical device. Preferably, the receiver is a mandrel which rotates about its axis so that a fibrous tubular shape is formed.

The operating conditions for electrostatic spinning will depend on the specific polymer chosen and the properties of the fabricated device desired. These conditions can be readily determined empirically. If a tubular structure is desired, and the receiver is a mandrel, then the electrical charge on the mandrel desirably ranges from about 8 to about 20 KV, preferably from about 10 to about 15 KV. If the charge is less than about 8 KV, then the electrostatic attraction may be insufficient to attract the polymer solution onto the mandrel. If the charge is greater than about 20 KV, then the strength of the electric current generated may cause the polymer to degrade.

In the preferred embodiment for the preparation of a biomedical device having a tubular shape, auxiliary electrodes are placed above and below the rotating mandrel to aid in directing the polymer discharged from the nozzles onto the mandrel. The electrical charge on the auxiliary electrodes desirably ranges from about 4 to about 15 KV, preferably from about 6 to about 10 KV.

Additionally, the surface temperature of the mandrel should be below the melting temperature of the polymer to avoid the spun fibers from fusing together. Preferably, the surface temperature of the mandrel is less than 110° C.

The polymer spun to prepare the biomedical device of this invention is a copolymer of a predominant amount of vinylidene fluoride and the balance being a second fluorinated hydrocarbon monomer. Preferably, the second monomer is trifluoroethylene or tetrafluoroethylene. A "predominant amount" of vinylidene fluoride refers to at least 50 weight percent of the monomer mixture from which the copolymer is derived. Advantageously, the amount of vinylidene fluoride in the monomer mixture from which the copolymer is derived ranges from about 50 to about 95 weight percent, preferably from about 60 to about 80 weight percent. If the amount of vinylidene fluoride is less than about 50 weight percent, then the biomedical device prepared from such a copolymer would most likely exhibit very limited or insignificant piezoelectric properties. If the amount of vinylidene fluoride is greater than about 95 percent, then the prepared device would likely require sequential stretching and poling to exhibit piezoelectric properties.

The weight average molecular weight of the copolymer, as determined by gel permeation chromatography, desirably ranges from about 30,000 to about 1,000,000. The preferred weight average molecular weight ranges from about 30,000 to about 500,000. A molecular weight less than about 30,000 will generally not provide the mechanical properties necessary to prepare a useable medical device. The crystallinity of the copolymer should range from about 20 to about 60 percent, as determined using conventional methods, e.g. hot stage microscopy, x-ray diffraction, or differential scanning calorimetry (DSC). Finally, the copolymer should consist of at least 90 percent head to tail monomer to monomer addition.

The particular copolymer chosen will depend, among other things, on the desired physical properties of the biomedical device and its desired degree of piezoelectricity. One preferred copolymer of vinylidene fluoride and tetrafluoroethylene which is available commercially is Kynar SL® copolymer.

The copolymer is advantageously dissolved in a compatible solvent to facilitate its spinning for the preparation of desirable fibrous structures. Suitable solvents include dimethylacetamide (DMAC), methyl ethyl ketone (MEK), ethyl acetate, dimethylformamide (DMF), methyl pyrrolidone, dimethylsulfoxide (DMSO), and triethylphosphate. The concentration of the copolymer in solution should range from about 10 to about 40 percent of the weight of the solution so as to provide a transparent, homogeneous solution having a viscosity effective for efficient spinning. The preferred solvent is DMAC.

Tubular structures prepared from the copolymer on a rotating mandrel are preferably corrugated. Certain methods exist for corrugating the spun copolymer which are made possible because of the crystallinity of the copolymer, and the method described in the following Example is illustrative. Corrugation improves the suppleness, compliance and kink resistance, properties which are especially important for vascular prothesis and neural prostheses.

The biomedical device of this invention can be spun from the copolymer simultaneously with other polymers. For example, a solution of the copolymer and a polyurethane can be spun to prepare novel medical devices combining the properties of each of the polymers.

The following Example is illustrative only and is not intended to limit the scope of the claimed invention. Numerous additional embodiments will become readily apparent to those skilled in this art.

EXAMPLE

1. The Copolymers

Two copolymers are used in this Example. The first copolymer is Kynar SL® copolymer, which is a copolymer of about 70 weight percent vinylidene fluoride and the balance tetrafluoroethylene. The second copolymer is a copolymer of about 70 weight percent vinylidene fluoride and the balance trifluoroethylene.

The copolymers are electrostatically spun from solution onto a rotating mandrel to form microfibrous, microporous fabrics in sheet form and in the form of hollow cylinders. The detailed process for carrying out the electrostatic spinning operation is described in U.S. Pat. No. 4,043,331.

The Gross and Microscopic Structure of the Microfibrous Copolymers

The materials spun from the two copolymers are indistinguishable, the surface of the material is featureless and smooth to the naked eye. The material is relatively stiff and in the tubular form, kinks easily.

Scanning electron microscopy reveals its microfibrous form. Fibres of 1.0 μm–4.0 μm are dispersed randomly and adhere at their points of contact. They are separated by spaces of irregular size and shape, but average approximately 7.0 μm across.

The Spinning Conditions Used for the Production of Cylindrical Tube of the Copolymers Each of the copolymers is dissolved in DMAC. The vinylidene fluoride/tetrafluoroethylene copolymer is a 25% wt. copolymer/wt. solution and the vinylidene fluoride/trifluroethylene copolymer is a 35% wt. copolymer/wt. solution.

Settings for the Spinning of Material Used for the Further Studies Described in this Report To produce a tube of 30 cms long, 6 mm internal Diameter, 0.4 mm wall thickness:

Mandrel operating length 30 cms

Diameter 6 mm

Mandrel rotation 1,000 r.p.m.

Charge on mandrel −12 Kv

Charge on Auxiliary electrodes −8.5 Kv

Manifold and Hollow Needles 5 needles—length 1½"

Bore—0.010"

Distance from needle tips to mandrel 2½"

Volume of solution used 6.0 ml

Rate of deposition of solution 4.0 ml/hour

Temperature of the environment within the enclosed rig 45° C.

Humidity—15%

Post-Spinning Treatment

The removal of sheet material is by cutting it from a mandrel of large diameter. The removal of intact tubes of the material from smaller mandrels requires the use of a specially prepared mandrel. A tubular sheath of thin metal foil is closely applied to the mandrel onto which the copolymer fibres are deposited electrostatically. The copolymer tube together with the metal foil will slide off the mandrel easily. The metal foil is then removed.

For some purposes e.g. nerve guides, it will be necessary for the tubes of the electrostatically spun tubes of the two piezoelectric polymers to be flexible. This can be achieved by fine crimping of the pre-formed tubes, the crimps lying in the circumferential direction.

The method used to create the crimps, or corrugations, is as follows:

A microfibrous tube is made, as described above, on a steel mandrel. A circular hole is made in thick sheet of 'plexiglas', acrylic plastic, so that the hole is only very slightly larger than the diameter of the mandrel. The exposed end of the steel mandrel is passed through the hole in the thick plastic sheet and is pushed through it, forcing the overlying covering of the microfibrous copolymer to crimp, reducing the length of the tube to one third of its original length. The crimped microfibrous tube is now heated to 90° C. for 30 minutes. It is allowed to cool on the mandrel. When pushed off the mandrel the new fibrous tube retains its corrugated form. On extension, lengthways to two third of its original length it retains it corrugations and is now flexible.

Uniaxial Tensile Properties of Electrostatically Spun Vinylidene Flouride/Tetrafluoethylene and Vinylidene Fluoride/Trifluroethylene Copolymers Tensile strength is taken as the peak load divided by the unstressed cross-sectional area of the specimen.

Strain at peak stress is the extension at peak load divided by the unstressed length of specimen.

Yield stress is the load at yield point divided by the unstressed cross-sectional area of specimen.

Physcial Properties of a Crimped Tubular Structure Fabricated from a Vinylidene Fluoride/trifluroethylene Copolymer

| | Longitudinal | Circumferential | Mean |
|---|---|---|---|
| Tensile strength ($\times 10^6$ Nm$^{-2}$) | 6.86 | 4.62 | 5.74 |
| Strain at Peak Stress | 1.73 | 2.31 | 2.02 |
| Youngs Modulus ($\times 10^6$ Nm$^{-2}$) | 4.12 | 0.91 | 2.51 |
| Yield Stress ($\times 10^6$ Nm$^{-2}$) | 3.16 | 2.24 | 2.7 |

Physical Properties of a Crimped Tubular Structure Fabricated from Kynar SL ® Vinylidene fluoride/tetraflurοethylene Copolymer

| | Longitudinal | Circumferential | Mean |
|---|---|---|---|
| Tensile strength ($\times 10^6$ Nm$^{-2}$) | 4.67 | 2.52 | 3.6 |
| Strain at Peak Stress | 1.22 | 1.28 | 1.25 |
| Youngs Modulus ($\times 10^6$ Nm$^{-2}$) | 2.17 | 0.27 | 1.22 |
| Yield Stress ($\times 10^6$ Nm$^{-2}$) | 4.2 | 1.12 | 2.66 |

3. The Experimental Evidence that Confirms the Acquisition of Piezoelectric Properties During the Process of the Creation of the Fibrous Fabric of the Two Copolymers Measurement of Surface Charge of Electrostatically-Spun Polyvinylidene Fluoride Tetrafluoroethylene Grafts The electric charge of non-crimped specimens, 6 mm internal diameter and 4 cm long is measured in an electric field meter (JC1 Model 111M) fitted with a Faraday pail. The attachment of the pail to the fieldmeter greatly simplified the measurement. To carry out a measurement, the specimen is introduced into the pail using insulated tweezers and the charge in picoCoulombs is displayed on a digital readout, Electrostatically spun polyvinylidene fluoride tetrafluoroethylene (PVTFE) is highly piezoelectric and the surface charge is affected by handling. Repeated handling with tweezers and transfer to the Faraday pail causes the electric charge to increase significantly. To minimize these effects, a silk suture was tied to one corner of the specimen. When transferring the specimen to the Faraday pail, the free end of the suture is held with tweezers and the specimen gently lowered into the pail.

To obtain a figure for the permanent charge on PVTFE grafts the specimen is placed on a conducting mesh and allowed to stand, in air, for about 48 hours prior to measurement. The charge for a 4 cm long specimen is −52 picoCoulomb or − 6.9 pC/cm$^2$.

Figure 2:
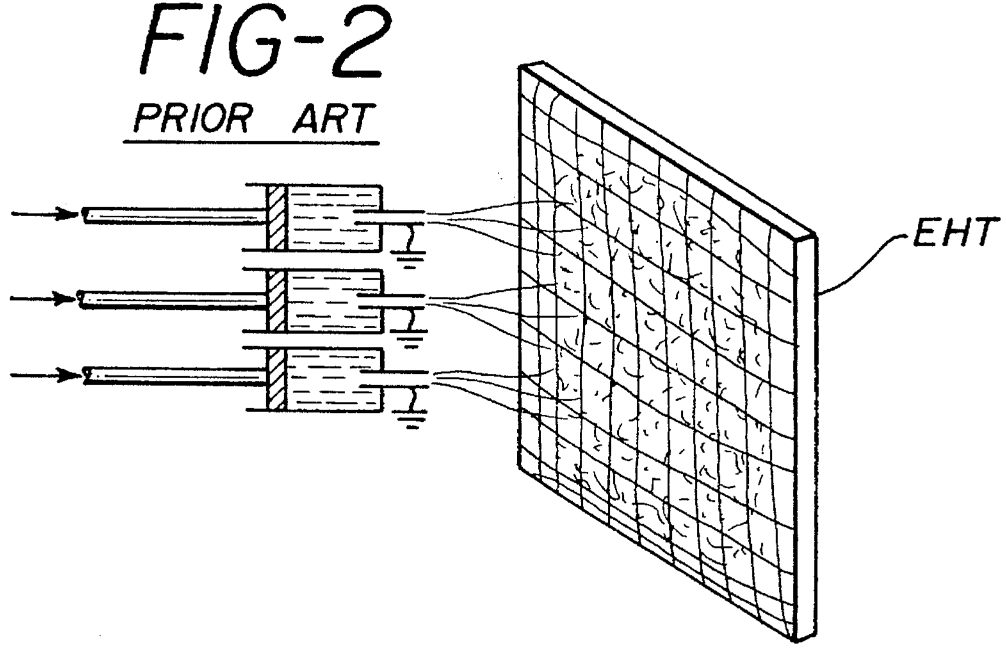
FIG. 2 is a schematic perspective view of a second embodiment of an electrostatic spinning and collecting apparatus.
Figure 3:
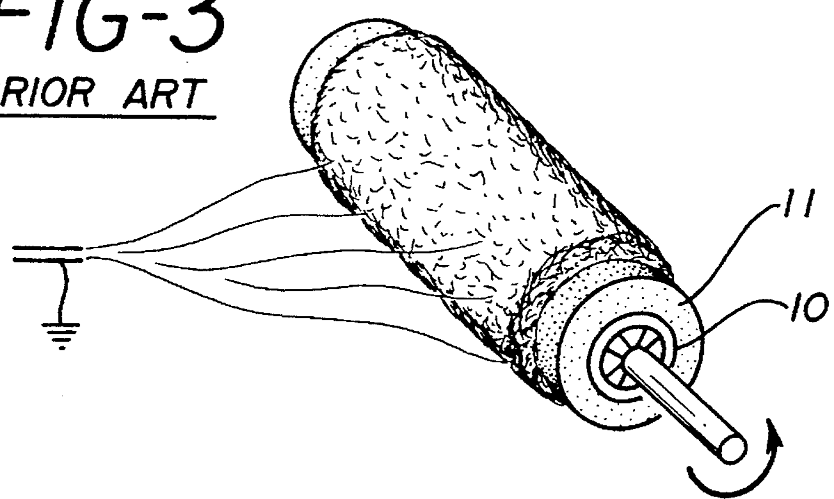
FIG. 3 is a schematic perspective view of a third embodiment of an electrostatic spinning and collecting apparatus. In this figure the collecting surface is a metal tube 10 have a sleeve 11 of flexible open-cell polyurethane foam.

The variation in electric charge with time is also determined. By manually bending the specimen (4 cm long) about 5 times a relatively large initial charge of approximately −400 pC is obtained. The change in this initial value is monitored over several hours and it is found that it is halved in about 5 hours. The charge is plotted against time (FIG. 2).

Grafts made on a positively charged mandrel generally gave values of charge slightly more negative than those made on a negatively charged mandrel (e.g. −475 pC initial charge for a +ve mandrel and −378 pC for a −ve mandrel).

The surface charge on polyvinylidene fluoride trifluoroethylene grafts is much higher than that on standard kynar fluorinated polymer, about −1 nC for a 4 cm long graft (133 $pC/cm^2$).

Because of the sensitivity of the material to handling, these values of charge should be used only as a guide. More work will be required to establish a common baseline from which to compare the different materials and the grafts made under different spinning conditions.

Measurement of Piezoelectric Current Induced by Pulsatile Pressure in Crimped Electrostatically Spun Polyvinylidene Fluoride Tetrafluoroethylene Grafts.

It has been shown that microporous tubes of polyvinylidene fluoride tetrafluoroethylene produced by electrostatic spinning is piezoelectric. Crude measurements showed that currents in the order of tens of picoamps could be produced when grafts 6 mm diameter and 25 cm long are repeatedly stretched.

In this study we report the preliminary experiments carried out to measure the piezoelectric currents generated in grafts 6.5 cm long subjected to physiological pressure loads over a frequency range of 0.2 to 12 Hz.

Materials and Methods

Six-millimeter diameter crimped grafts are used in this study. Since the material is porous a thin silicone rubber layer is deposited on the inner surface to make the graft watertight.

The electrodes consisted of two platinum strips, about 1.0 to 1.5 mm wide and 30 mm long, wrapped around the graft, approximately 6 mm from each end. The strips are bonded to the outside surface of the graft using silver-leaded epoxy. One end of the graft is plugged while the other is joined to a connector which housed a catheter-lip pressure transducer. On this connector is provided a side port which communicated with the graft lumen. A sinusoidal pressure can be applied through this side part by joining it to a diaphragm pulsatile pump via a short length of plastic tubing.

The graft is carefully primed with distilled water to ensure that all air is dislodged from the lumen. It is then mounted in a specimen chamber. A longitudinal extension of 20% is applied before the graft is pressurized. The pressure amplitude is set to the normal physiological value of 40 mm Hg and the frequency is varied in discrete steps from 0.2 to 12 Hz.

The current across the platinum electrodes are measured by means of a picoammeter, configured in feedback mode (Keithley 418). Both present and current signals are recorded on a chart recorder.

Results and Discussion

For a tubular specimen subjected to physiological loading three components of piezoelectric current may be measured; namely, the radial, circumferential and longitudinal components. In these preliminary experiments, a simple electrode configuration is employed to allow the longitudinal component of current to be obtained.

The following general observations are made:

1. Due to the length changes in the graft during pressurization, a current is produced with each pressure pulse.

2. The fundamental frequency of this current is the same as that of the applied pressure waveform. There is a phase shift between the current and pressure waveforms and it changes with frequency.

3. At low frequencies the current waveform is highly distorted. As frequency is increased the distortion becomes less marked. The distortion is probably an artifact and may be caused by inadequate bonding of the electrodes in the graft surface. Because of the crimps, and insufficient amount of applied longitudinal extension may cause lateral as well as axial movements of the graft during pressurization and this may result in the current waveform distortion.

4. The amplitude of the piezoelectric current increases with the frequency of applied pressure. That is, the faster the rate of loading, the larger the piezoelectric current.

5. When the mean pressure and the initial longitudinal extension is applied, a small negative current is observed on the picoammeter. However, this current decays to zero within a relatively short period. Static pressure of longitudinal extension, therefore, does not produce a piezoelectric response.

6. The current waveform oscillates about the zero line, that is, during half the cycle the current is negative and the other half it is positive.

7. At a frequency of 1 Hz, the total charge per pulse in the graft varies from +10 to −10 picoCoulomb.

I claim:

1. A biomedical device selected from the group consisting of a vascular prothesis, a neural prosthesis and a wound dressing exhibiting piezoelectricity prepared by electrostatically spinning under suitable conditions for the formation of piezoelectric fibers a copolymer suitable for direct contact with bodily fluids of a living organism of the following comonomers:

a) from in the range of from about 50 to about 95 weight percent of vinylidene fluoride, and b) a second fluorinated hydrocarbon, selected from the group consisting of trifluoroethylene and tetrafluoroethylene, and collecting the spun fibers on a suitable receiver.

2. The device of claim 1 wherein the amount of vinylidene fluoride is between about 60 and about 80 weight percent.

3. The device of claim 2 wherein the weight average molecular weight of the copolymer is between about 30,000 and about 1,000,000.

4. The device of claim 3 wherein the weight average molecular weight of the copolymer is between about 50,000 and about 500,000.

5. The device of claim 4 wherein the copolymer exhibits a crystallinity of between about 20 and about 60 percent.

6. The device of claim 5 in the form of a fibrous mat or sheet.

7. The device of claim 5 wherein the device has a tubular structure.

8. The device of claim 7 wherein the tubular structure is corrugated.

* * * * *